United States Patent
Davis

(10) Patent No.: US 6,726,645 B1
(45) Date of Patent: Apr. 27, 2004

(54) DYNAMIC RESPONSE ANKLE-FOOT ORTHOSIS

(76) Inventor: Locke Davis, 1122 1/2 Dartmouth St., Apt. 2, Chattanooga, TN (US) 37405

( * ) Notice: Subject to any disclaimer, the term of this patent is extended or adjusted under 35 U.S.C. 154(b) by 0 days.

(21) Appl. No.: 09/878,621

(22) Filed: Jun. 11, 2001

Related U.S. Application Data

(62) Division of application No. 09/405,074, filed on Sep. 27, 1999, now Pat. No. 6,334,854.

(51) Int. Cl.$^7$ .................................................. A61F 5/00
(52) U.S. Cl. .............................. 602/27; 602/23; 602/5; 602/6; 602/7; 602/8; 602/65
(58) Field of Search ............................. 602/5–8, 23, 27, 602/65; 264/222–223, DIG. 30

(56) References Cited

U.S. PATENT DOCUMENTS

| | | | | |
|---|---|---|---|---|
| 3,814,088 A | * | 6/1974 | Raymond | 602/27 |
| 4,193,395 A | * | 3/1980 | Gruber | 602/6 |
| 4,286,586 A | * | 9/1981 | Potts | 602/6 |
| 4,888,225 A | * | 12/1989 | Sandvig et al. | 428/71 |
| 5,154,690 A | * | 10/1992 | Shiono | 602/5 |
| 5,624,386 A | * | 4/1997 | Tailor et al. | 602/6 |
| 5,897,515 A | * | 4/1999 | Willner et al. | 602/27 |
| 6,146,344 A | * | 11/2000 | Bader | 602/6 |
| 6,334,854 B1 | * | 1/2002 | Davis | 602/6 |

* cited by examiner

Primary Examiner—Nicholas D. Lucchesi
Assistant Examiner—L Amerson
(74) Attorney, Agent, or Firm—Stephen J. Stark; Miller & Martin LLP

(57) ABSTRACT

An orthotic device is developed and customized to control the desired movement of a patient's defective lower limb. The device incorporates a footplate made of a rubber-like elastomeric material and a proximal segment that encompasses the foot at the metatarsophalangeal joints and the shin portion of the leg. This proximal segment is made of a rubber-like elastomeric material laminated into multiple layers of fabric throughout the proximal segment. Additional strips of fabric are positioned within the proximal segment of the device to limit or promote certain motions within the foot and ankle.

19 Claims, 4 Drawing Sheets

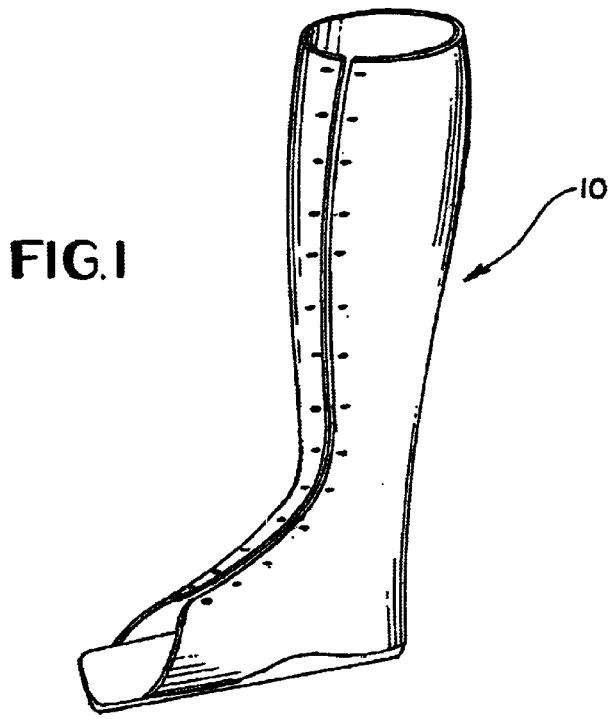
FIG. 1
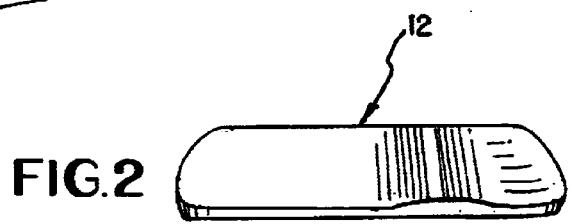
FIG. 2
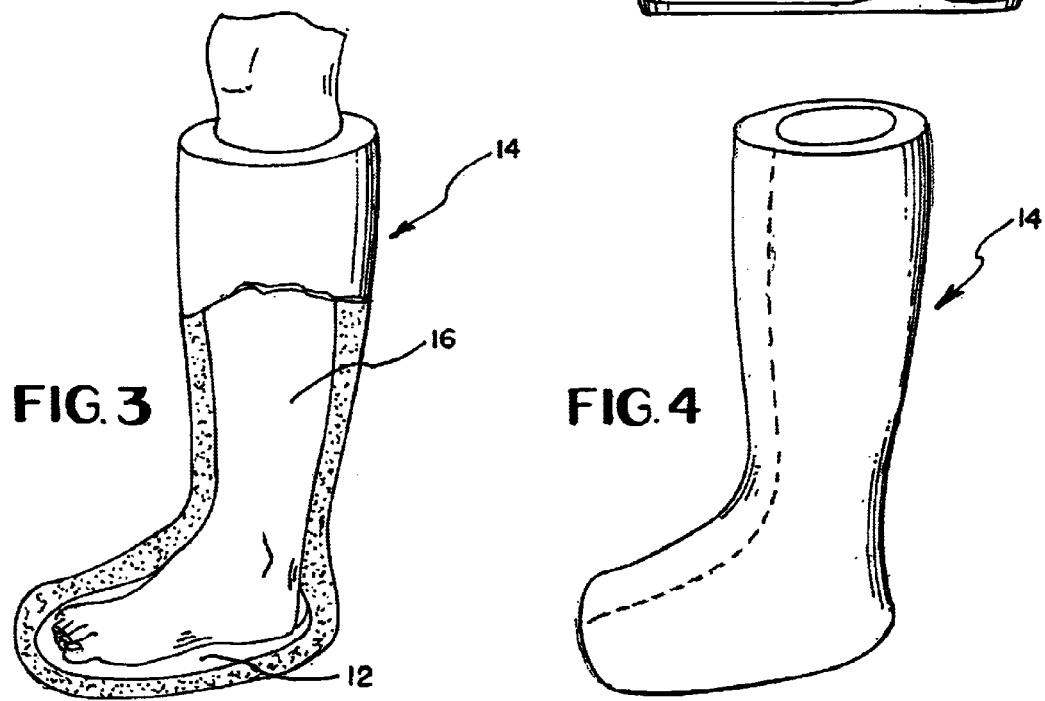
FIG. 3
FIG. 4

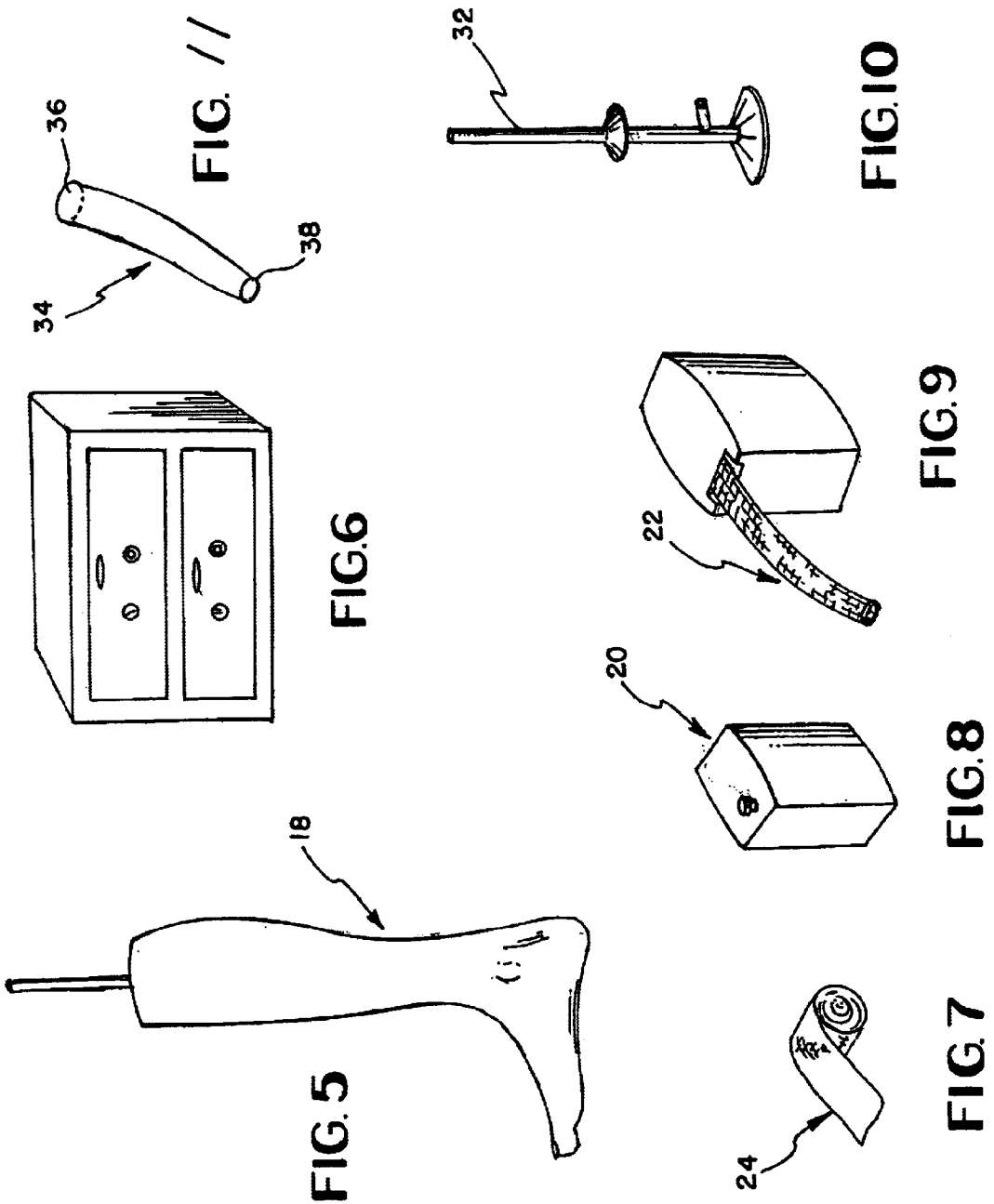

DYNAMIC RESPONSE ANKLE-FOOT ORTHOSIS

This application is a divisional application of Ser. No. 09/405,074 U.S. Pat. No. 6,334,854 filed Sep. 27, 1999.

BACKGROUND OF THE INVENTION

Ankle foot orthosis are commonly used as foot, ankle, and leg braces for improving movement. Years ago a leg brace would consist of two metal bars and a stirrup attached to the sole of the shoe. A horizontally positioned padded, metal band, contoured to the back of the leg calf, would connect the two metal bars. A broad strap across the anterior section of the calf would hold the brace in place. This type of brace has limited use today but is not considered to be state of the art orthotic management. This type of device lacks biomechanical control of the foot and ankle and is also cumbersome and heavy.

The ankle foot orthosis, being a device that applies biomechanical forces to a body segment, is usually fabricated from thermoplastics. The thermoplastic is heat molded over a positive mold similar in shape to the patient's limb, then cooled, trimmed and often creates rigid or semirigid laminates. Ankle joint motion in the orthotic device is often provided by a mechanical hinge type joint at the ankle joint location.

There are some existing fundamental problems of orthotic management. A rigid orthosis, which does not allow plantarflexion of the ankle, will also prevent extension of the hip and knee and causes instability in the hip and knee. Balance at the foot-ankle complex cannot develop because activity and sensation of movement is limited with resultant muscle wasting.

Current orthotic technology does not allow for the triplanar activity of the foot and ankle in stance phase found in normal gait. The use of very thin or more flexible plastics has been used to allow more motion in the foot and ankle. However, much of the benefit of wearing an orthosis is lost, when significant control is needed for spastic muscle activity or pathomechanical deformities. Then stability is reduced to allow mobility. Allowing motion is not the same as promoting and controlling more normal motion. The enclosed disclosure promotes and controls more normal motion.

For many patients who require the use of an ankle-foot orthosis, current orthotic technology does not adequately address the dynamic changes that occur in the foot and ankle complex during the gait cycle. Triplanar motion of the foot and ankle requires a dynamic response. Current technology positions the segments of the foot in a static position or allows motions to occur by reducing the corrective forces. While the use of a mechanical ankle joint may provide motion of the talocrural joint in the sagittal plane, complex motions, required within the foot, are restricted from a normal biomechanical response because of the static forces applied by the brace. Optimal orthotic management should control abnormal motion by restricting specific motion during specific events of the gait cycle. This cannot be achieved by holding the segments of the foot in an uniformed position throughout the gait cycle. The foot must remain a mobile entity that engages in the normal activity of gait, but is prevented from abnormal motion. Because the needs of the corrective forces of the foot and ankle complex differ within different events of the gait cycle, the ankle-foot orthosis should be dynamic in its application of corrective forces.

In this way a more normal gait pattern can be obtained with less compensatory activity required by proximal segments of the body. This invention, with its pliable dynamically responding ankle-foot orthosis, provides predetermined corrective forces on the foot and ankle complex during different events of the gait cycle.

SUMMARY OF THE INVENTION

The purpose of this invention is to provide an improved method of controlling the movement of a patient's defective lower limb. The method provides, with its strategically placed strips, an improved system of constructing a customized ankle-foot orthosis, based on the combination of the physical therapy assessment and the orthotic evaluation in determining designed characteristics needed for controlling the defective lower limb movement.

Various other features of the method of the present invention will become obvious to those skilled in the art upon reading the disclosure set forth hereinafter.

BRIEF DESCRIPTION OF DRAWINGS

Referring now to the drawings, the system is illustrated in views of various stages of its development, equipment and its finished product:

FIG. 1 is a top perspective view of the device used to control lower limb movement;

FIG. 2 is a top perspective view of a contoured footplate used for lower limb support;

FIG. 3 is a cut-away view of the lower limb positioned in a plaster cast;

FIG. 4 is a perspective view of the plaster cast with the lower limb removed and positioned to receive molding plaster;

FIG. 5 is a side perspective view of the lower limb mold after removal of the plaster case;

FIG. 6 is a perspective view of an oven used for heat curing;

FIG. 8 is a perspective view of a container of elastomeric resin;

FIG. 9 is a perspective view of a container of nylon stockinette material;

FIG. 10 is a perspective view of a vacuum attachment;

FIG. 11 is a perspective view of a PVA sleeve;

DETAILED DESCRIPTION

Figure 12:
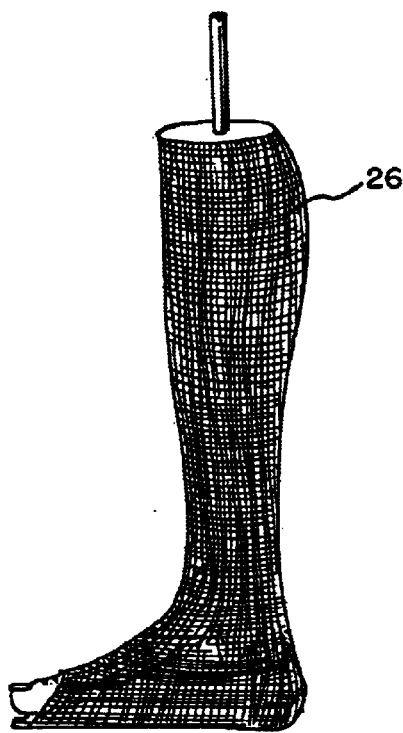
FIG. 12 is a side perspective view of layers of nylon stockinette positioned over the lower limb mold.

Referring now to FIG. 1, there is illustrated an isometric view of the orthosis 10 that is custom built to fit it's subject, is light weight and highly flexible and is used to contain and control the movement of a patient's defective lower limb.

The method of control calls for an orthotic evaluation of the patient's lower limb, for determining the needed adjustment and control that would benefit the patient's walk and lower limb movement. Based on the evaluation, a mold of the patient's lower limb is needed to produce the laminated device that produces the method of control.

A footplate 12, FIG. 2, being developed from a rubber-like elastomeric material, is designed and contoured to fit and support the plantar surface of the patient's foot. A plaster cast 14, see cut-a-way view of FIG. 3, is then made of the patient's lower limb 16 with the foot positioned on the footplate 12. After sufficient hardening, the patient's lower limb 16 is removed, leaving the plaster cast 14, FIG. 4, with the footplate 12 remaining in the cast. The plaster cast 14 is then filled with molding plaster to create a mold of the patient's lower limb. The footplate 12 correctly shapes the plantar foot surface of the mold.

After the plaster mold has hardened sufficiently, the outer cast 14, with the footplate 12, is removed and any adjustment of the mold's surface and the toeplate can be corrected by applying or removing needed plaster, thus creating a plaster mold 18 of the patient's lower limb, FIG. 5. To insure proper curing, the mold 18 is allowed drying time in a low temperature oven, FIG. 6. The lower limb plaster mold 18 is the treated by saturating it's entire surface with a rubber-like elastomeric resin 20, FIG. 8, over which at least two layers of nylon stockinette 22 are applied, FIG. 9 and 12.

Strips 28 made of KEVLAR(™) or other aramid fabric, 24 see FIG. 7, of selected width and with light adhesive, is attached in specific selected patterns to the set-ups stockinette surface 26 to create and control predetermined lower limb movement patterns, as determined by the orthotic evaluation for needed adjustment and control. By adjusting the arrangements of the strips 24, various adjustments in the leg and foot movement are created, yet leaving the orthosis light and highly flexible.

Figure 14:
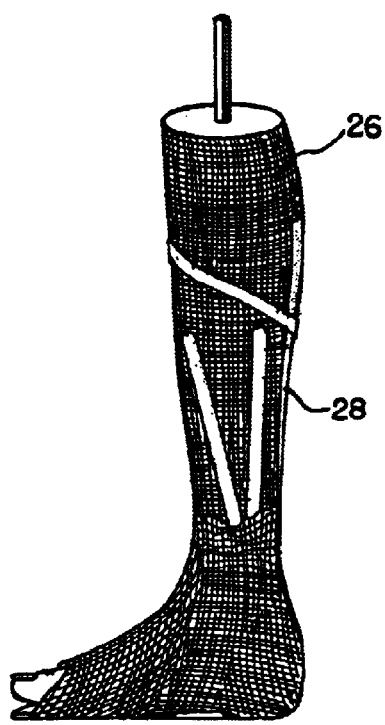
FIG. 14 is a side perspective view of additional layers of stockinette material positioned over the strips and underlying stockinettes.

At least two more layers 30 of stockinette material 22 are then applied over the strips 28 of the set-up, see cut-a-way view of FIG. 14. The set-up is then positioned onto a vacuum stand 32, FIG. 10, and covered with a dampened PVA sleeve 34, FIG. 11, having it's upper end 36 closed and its lower 38 opening sealed to the vacuum stand 32, thus allowing a sufficient vacuum to occur between the outer surface of the set-up and the PVA sleeve 34, to enhance drying.

Figure 15:
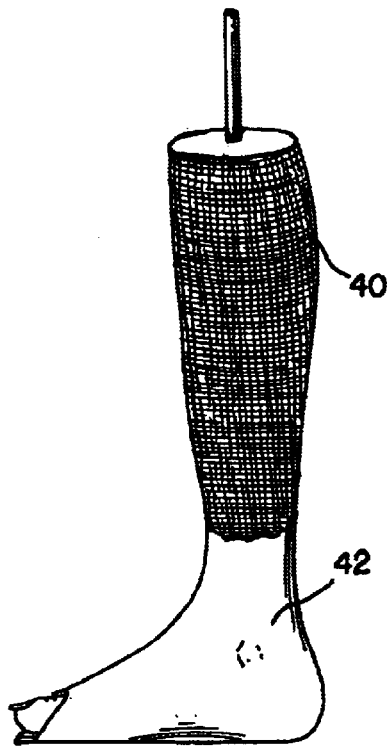
FIG. 15 is a cut-a-way view of the outside application of the elastomeric resin.
Figure 17:
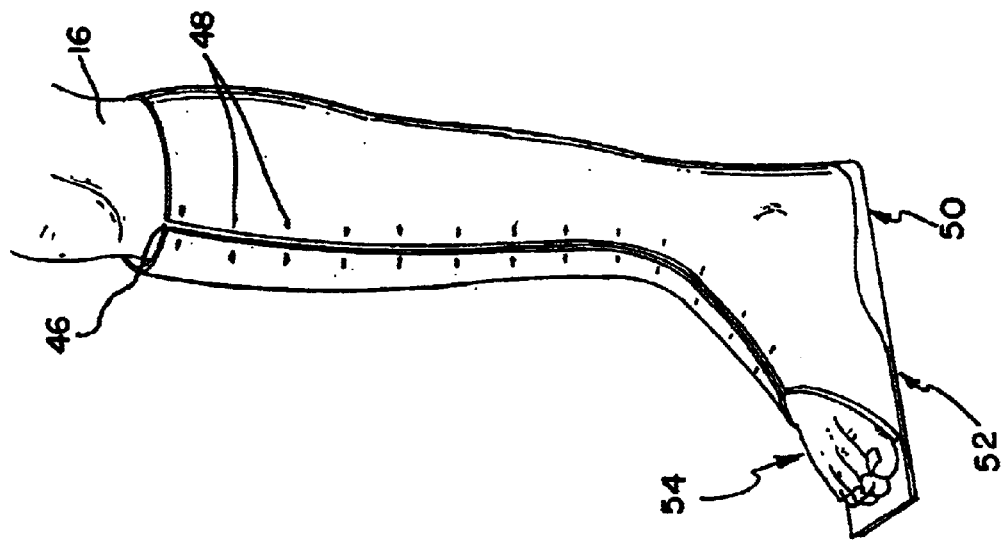
FIG. 17 is a top perspective view of the laminated mold set-up fitted on the patient's lower limb and in a position for lacing or closing.
Figure 16:
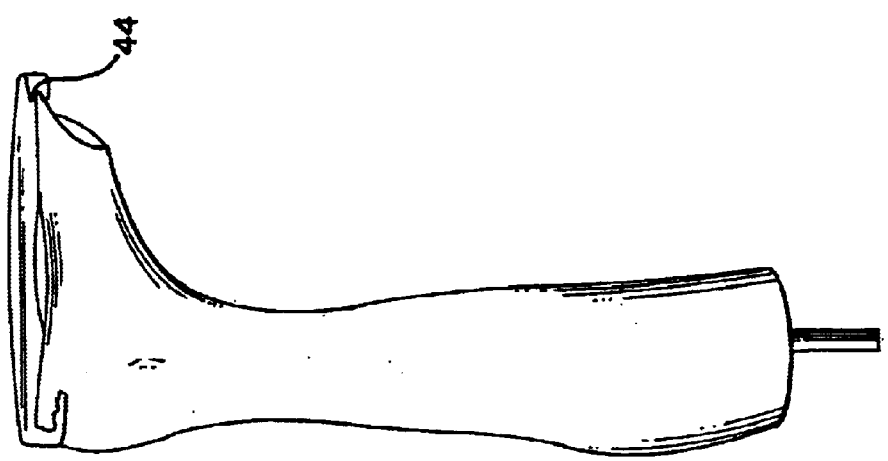
FIG. 16 is an inverted side perspective view of the laminated mold set-up in an inverted position for building up the plantar surface.

The upper ends 34 of the PVA sleeve 34 is then opened and elastomeric resin is uniformly applied to the stockinette fabric set-up 40 (see cut-a-way view of FIG. 15). FIG. 15 illustrates the stockinette fabric set-up along the calf portion in the cut-away portion and the outer finish 42 of the applied elastomeric resin, as applied uniformly under vacuum drying along the foot portion. After completing the resin application uniformly, the upper end 36 of the PVA sleeve 34 is re-closed to allow set-up-drying time under vacuum, then heat-cured for a sufficient time under selected heat. The laminated set-up is then soaked in hot water with the PVA washed from the lamination. After drying, the laminated set-up's plantar surface of the foot section is sanded, until the fibers of the nylon stockinette are exposed. The set-up is then positioned in an inverted position with the plantar foot section in a horizontal position, FIG. 16. A dam is built of selected height, around the border of the foot with masking tape 44, see cut-a-way view of FIG. 16. The plantar surface is then filled to a selected depth with elastomeric resin and allowed sufficient curing time, then heat cured. The masking tape 44 is then removed and excessive material is sanded away. A center dividing line is cut down the front of the laminated set-up device, then removed from its mold and selectively trimmed. Continuous closing means 48 are constructed in series down each side of the laminated set-up anterior opening 46 or placket. FIG. 17 illustrates the orthosis apparatus 10 containing the patient's lower limb 16, and positioned to receive lacing or other selected means of continuous closings, thus establishing a method of controlling the movement of a patient's lower limb 16.

A patient with a defective lower limb 16 is evaluated by the Orthotic Doctor and determined certain corrective movements are needed to benefit the patient's walk and lower limb movement. The method used to benefit the patient's movement is to create and construct a lower limb encasement or boot that would be light and flexible and only allow movement that would coincide with a predetermined established pattern. To create and construct this encasement, an orthosis 10 a plaster mold 18, duplicating the patient's lower limb, is made.

Figure 13:
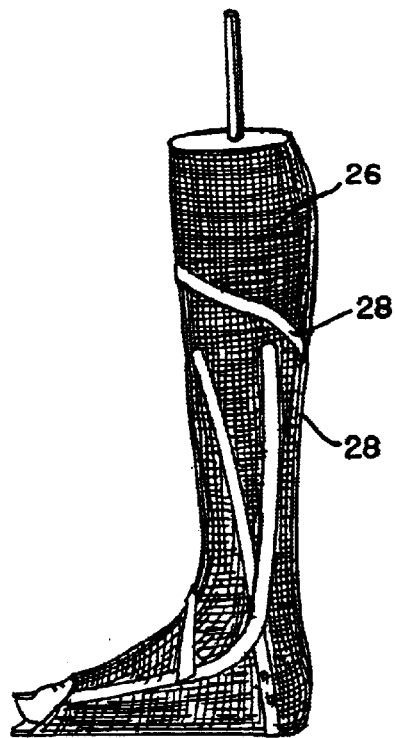
FIG. 13 is a side perspective view of strategically placed strips positioned in various patterns over the stockinette material.

The mold 18 is covered, until saturated, over its entire outer surface with a rubber-like elastomeric resin, over which at least two layers 26 of nylon stockinette 28 are applied, FIG. 12. Strips 28 of selected width and with light adhesive are applied to the stockinette 26 in specific predetermined patterns that will only allow selected movements of the patients lower limb 16, see FIG. 13. At least two additional layers of stockinette material 22 is then applied over the existing set-up and it's strips 28, see cut-a-way view of FIG. 14. The mold, being inverted onto a vacuum stand 32, is covered with a dampened PVA sleeve 34 and positioned for a sufficient vacuum to occur between the mold surface and the PVA sleeve 34, for drying the rubber-like elastomeric resin that is applied uniformly over the fabric set-up. After curing and low oven drying, the PVA is washed from the laminated set-up and the set-up is placed in an inverted position, with the foot horizontal, to allow the construction of a dam made with masking tape 44 around the foot border, so that elastomeric resin can be applied to the foot plantar surface. After heat curing and removing the masking tape 44, excessive material is sanded away until the fabric becomes exposed at the base of the heel section 50 and at the heads of the metatarsal section 52 and a center dividing line is cut down the front of the laminated set-up and then removed from the mold 18. Surplus lamination material is trimmed away at the toe section 54 and closing means 48 are constructed in series on each side of the anterior opening 46, thus the orthosis 10 is created for controlling the movement of the patient's defective lower limb 16.

It is to be understood that the foregoing drawings and description of the invention is to be taken as a preferred embodiment and that various other modifications will occur to those skilled in the art upon reading the disclosure, however all changes and modifications that come within the spirit of the invention are desired to be protected.

What is claimed is:

1. An ankle foot orthosis for use with an ankle and foot of a patient, said orthosis comprising:
   a laminated set-up having
   a) at least one first fabric layer;
   b) at least one fabric strip placed in a specific pattern over the at least one fabric layer which assists in providing a predetermined lower limb movement; and
   c) a elastomeric resin impregnated into the at least one fabric layer and covering the at least one strip to provide an elastomeric laminate set up; wherein said laminated set up is sized to substantially surround a portion of the foot and the ankle of the patient, said laminate set up configured to follow the contour of a portion of the lower limb, ankle and the foot; and said laminated set up allowing motion except where restrained by the at least one fabric strip when in tension.

2. The ankle foot orthosis of claim 1 wherein the at least one first fabric layer is comprised of a stockinette material.

3. The ankle foot orthosis of claim 2 wherein the stockinette material is comprised of nylon.

4. An ankle foot orthosis for use with an ankle and foot of a patient, said orthosis comprising:
   a laminated set-up having
      a) at least one first fabric layer;
      b) at least one fabric strip placed in a specific pattern over the at least one fabric layer which assists in providing a predetermined lower limb movement; and
      c) a elastomeric resin impregnated into the at least one fabric layer and covering the at least one strip to provide an elastomeric laminate set up; wherein said laminated set up is sized to substantially surround a portion of the foot and the ankle of the patient, said laminate set up configured to follow the contour of a portion of the lower limb, ankle and the foot; and
   said laminated set up allowing motion except where restrained by the at least one fabric strip when in tension,
   wherein the laminated set up further comprises at least one second fabric layer over the at least one fabric strip and the elastomeric resin is further laminated into the at least on second fabric layer.

5. The ankle foot orthosis of claim 4 wherein the at least one second fabric layer is comprised of a stockinette material.

6. The ankle foot orthosis of claim 1 further comprising at least one of an arch support and a foot support positioned to be located below a plantar section of the foot.

7. The ankle foot orthosis of claim 6 wherein the at least one of the arch support and the foot support is comprised of an elastomeric material.

8. An ankle foot orthosis for use with an ankle and foot of a patient, said orthosis comprising:
   a laminated set-up having
      a) at least one first fabric layer;
      b) at least one fabric strip placed in a specific pattern over the at least one fabric layer which assists in providing a predetermined lower limb movement; and
      c) a elastomeric resin impregnated into the at least one fabric layer and covering the at least one strip to provide an elastomeric laminate set up; wherein said laminated set up is sized to substantially surround a portion of the foot and the ankle of the patient, said laminate set up configured to follow the contour of a portion of the lower limb, ankle and the foot; and
   said laminated set up allowing motion except where restrained by the at least one fabric strip when in tension, and
   a placket, wherein said placket allows the orthosis to be positioned about the ankle and foot of the patient.

9. The ankle foot orthosis of claim 8 further comprising closing means to substantially close said placket for the orthosis to substantially surround said ankle and foot portion of said patient.

10. The ankle foot orthosis of claim 8 wherein the placket extends from a top of a shin portion of the orthosis substantially vertically to a top portion of an ankle portion and then substantially horizontally to an end of a toe portion of the orthosis.

11. The ankle foot orthosis of claim 1 wherein the at least one fabric strip utilized for movement control of the lower limb is adhered to the at least one first fabric layer.

12. An ankle foot orthosis for use with an ankle and foot of a patient, said orthosis comprising:
   a laminated set-up having
      a) at least one first fabric layer;
      c) at least one aramid fabric strip placed in a specific pattern over the at least one fabric layer which assists in providing a predetermined lower limb movement;
      by restraining motion when in tension while allowing motion when placed in compression; and
      d) an elastomeric resin laminated into the at least one fabric layer and the at least one strip, to provide a laminated set up
   wherein said laminated set up is configured to substantially enclose a portion of the foot and the ankle of the patient, said laminate set up configured to follow the contour of a portion of the lower limb, ankle, and foot, and said laminated set up allowing motion except where restrained by the at least one fabric strip when in tension.

13. The ankle foot orthosis of claim 12 further comprising at least one of an arch support and a foot plate connected to a plantar foot section.

14. The ankle foot orthosis of claim 13 wherein the at least one of the arch support and the foot plate is comprised of an elastomeric material.

15. A laminated set up comprising at least one first fabric layer, at least one fabric strip placed in a specific pattern over the at least one fabric layer which assists in providing a predetermined lower limb movement, and an elastomeric resin laminated into the at least one fabric layer and the at least one strip, providing a laminated set up wherein said laminated set up is configured to substantially enclose a portion of the foot and the ankle of the patient, said laminated set up formed by the process comprising:
   a) creating a mold of a lower leg of patient;
   b) establishing the at least one first fabric layer over a portion of the mold;
   d) placing said at least one fabric strip in said specific pattern over the at least one first fabric layer;
   e) placing said at least one second fabric layer over the at least one fabric strip and said at least one first fabric layer;
   f) establishing an elastomeric laminate set up through the at least one second fabric layer into the at least one first fabric layer by impregnating the first and second fabric layers with an elastomeric resin to complete the laminated set up; and
   g) removing the laminated set up from mold for use on a lower limb of a patient wherein said laminated set up allows motion when worn by a patient except where and when the at least one fabric strip is placed in tension.

16. A laminated set up comprising at least one first fabric layer, at least one fabric strip placed in a specific pattern over the at least one fabric layer which assists in providing a predetermined lower limb movement, and an elastomeric resin laminated into the at least one fabric layer and the at least one strip, providing a laminated set up wherein said laminated set up is configured to substantially enclose a portion of the foot and the ankle of the patient, said laminated set up formed by the process comprising:

a) creating a mold of a lower leg of patient;

b) establishing the at least one first fabric layer over a portion of the mold;

d) placing said at least one fabric strip in said specific pattern over the at least one first fabric layer;

e) placing said at least one second fabric layer over the at least one fabric strip and said at least one first fabric layer;

f) establishing an elastomeric laminate set up through the at least one second fabric layer into the at least one first fabric layer by impregnating the first and second fabric layers with an elastomeric resin to complete the laminated set up; and g) removing the laminated set up from mold for use on a lower limb of a patient wherein said laminated set up allows motion when worn by a patient except where and when the at least one fabric strip is placed in tension and providing a placket along a portion of the set up, wherein said placket allows for the set up to be placed about the lower limb of the patient and said placket is adapted to close to substantially surround the lower limb.

17. The laminated set up of claim 16 wherein the placket extends along a cut from a top of a shin portion of the set up to a top of a toe portion of the set up.

18. The laminated set up of claim 15 further comprising the step of providing closure means to secure the set up about the lower limb of a patient.

19. The laminated set up of claim 15 further comprising the step of installing at least one of an arch support and a foot support on the planter foot section of the set up.

* * * * *